(12) United States Patent
Haidukewych

(10) Patent No.: US 6,440,131 B1
(45) Date of Patent: Aug. 27, 2002

(54) ACETABULAR BONE PLATE

(75) Inventor: George J. Haidukewych, Rochester, MN (US)

(73) Assignee: Mayo Foundation For Medical Education And Research, Rochester, MN (US)

( * ) Notice: Subject to any disclaimer, the term of this patent is extended or adjusted under 35 U.S.C. 154(b) by 0 days.

(21) Appl. No.: 09/932,485

(22) Filed: Aug. 17, 2001

Related U.S. Application Data

(60) Provisional application No. 60/274,906, filed on Mar. 9, 2001.

(51) Int. Cl.[7] .............................................. A61B 17/68
(52) U.S. Cl. ........................................... 606/60; 606/69
(58) Field of Search ..................................... 606/69, 60

(56) References Cited

U.S. PATENT DOCUMENTS

| | | | |
|---|---|---|---|
| 3,955,567 A | | 5/1976 | Richmond et al. |
| 4,454,876 A | * | 6/1984 | Mears |
| 4,573,458 A | * | 3/1986 | Lower |
| 4,651,724 A | * | 3/1987 | Berentey et al. |
| 4,762,122 A | * | 8/1988 | Slocum |
| 4,800,874 A | * | 1/1989 | David et al. ................... 606/69 |
| 5,015,248 A | | 5/1991 | Burstein et al. |
| 5,314,490 A | | 5/1994 | Wagner et al. |
| 5,326,367 A | * | 7/1994 | Robioneck |
| 5,746,742 A | | 5/1998 | Runciman et al. |
| 5,752,958 A | | 5/1998 | Wellisz |
| 5,785,712 A | | 7/1998 | Runciman et al. |
| 5,853,413 A | * | 12/1998 | Carter et al. |
| 5,904,684 A | * | 5/1999 | Rooks ........................ 606/69 |
| 5,951,557 A | | 9/1999 | Luter |
| 6,001,099 A | | 12/1999 | Huebner |
| 6,004,353 A | | 12/1999 | Masini |
| 6,221,073 B1 | * | 4/2001 | Weiss et al. .................. 606/60 |

FOREIGN PATENT DOCUMENTS

| | | | | |
|---|---|---|---|---|
| DE | 2410057 B1 | * | 7/1975 | |
| DE | 3442004 C | * | 4/1986 | ................... 606/69 |
| SU | 1827209 A1 | * | 6/1990 | ................... 606/69 |

* cited by examiner

Primary Examiner—Jeffrey A. Smith
(74) Attorney, Agent, or Firm—Quarles & Brady, LLP

(57) ABSTRACT

An acetabulum bone plate includes a central, support portion which is shaped to cover the posterior wall of the acetabulum and a pair of tabs which extend therefrom and attach to the pelvis. Spikes formed on the underside of the central portion engage bone fragments and fix them in place when fragment screws that extend through openings in the central portion are tightened. The fragment screws are angled away from the hip joint.

9 Claims, 3 Drawing Sheets

ACETABULAR BONE PLATE

RELATED PATENT APPLICATIONS

This application is based on U.S. Provisional Application Ser. No. 60/274,906 filed on Mar. 9, 2001 and entitled "Acetabular Bone Plate".

BACKGROUND OF THE INVENTION

The field of the invention is implantable plates which are attached to damaged or diseased bones, and more particularly, to bone plates attached to the surface of the pelvis.

A bone plate is a plate that is fastenable to the surface of a bone to immobilize a fracture in the bone or to support and stabilize a diseased region of the bone. The plate is typically made of a surgical grade metal such as stainless steel or titanium which has a very high tensile strength. The plate may be shaped to fit the contour of specific bone surfaces as described in U.S. Pat. Nos. 4,454,876; 4,800,874; 5,904,684 and 6,004,353, or the bone plate may be shaped by the surgeon during the operation as described in U.S. Pat. Nos. 4,573,458; 5,746,742 and 5,785,712. The bone plate is typically attached to the bone with screws that pass through judiciously placed holes in the plate.

The acetabulum is a circular-shaped ridge, or wall, of bone that defines a socket for receiving the semi-spherical head of the femur to form the hip joint. The most common fracture of the acetabulum is in its posterior wall. Multiple fractures forming small wall fragments are often found, and these multiple bone fragments must be fixed. This is currently done by cutting and bending multiple bone plates to fix the multiple bone fragments in place. This is a lengthy and challenging procedure for the surgeon. In addition, because the acetabulum wall forms part of a working joint, care must be taken when fastening each bone plate in place that none of the screws pass into the joint itself and interfere with joint operation.

SUMMARY OF THE INVENTION

The present invention is a bone plate which is shaped to fit the surface of the posterior acetabulum wall for fixing fractures therein. More particularly, the shaped bone plate includes a central portion which is shaped to fit directly over the posterior wall of the acetabulum and narrower tabs which extend in opposite directions from the central portion. Openings are provided in the central portion and the tabs for receiving mounting screws, and the openings in the central portion are shaped to guide screws away from the hip joint. Spikes are formed on the underside of the central portion to engage and fix multiple bone fragments.

A general object of the invention is to provide a bone plate which can be used to fix fractures of the posterior acetabulum wall. The wide central portion of the bone plate provides support in the fracture zone and the tabs hold it firmly in place. Multiple bone fragments are fixed to the bone plate by screws passing through openings in the central portion and spikes on its underside.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 2:
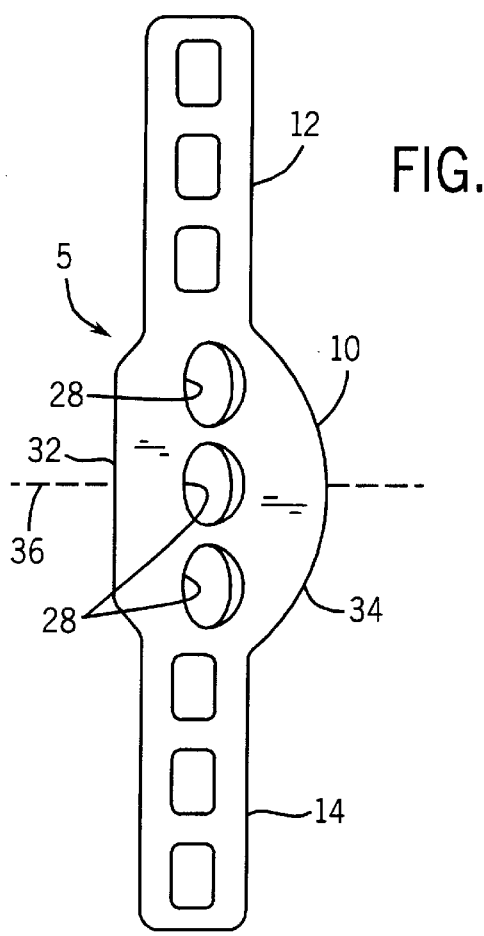
FIG. 2 is a top view of the bone plate in FIG. 4.
Figure 3:
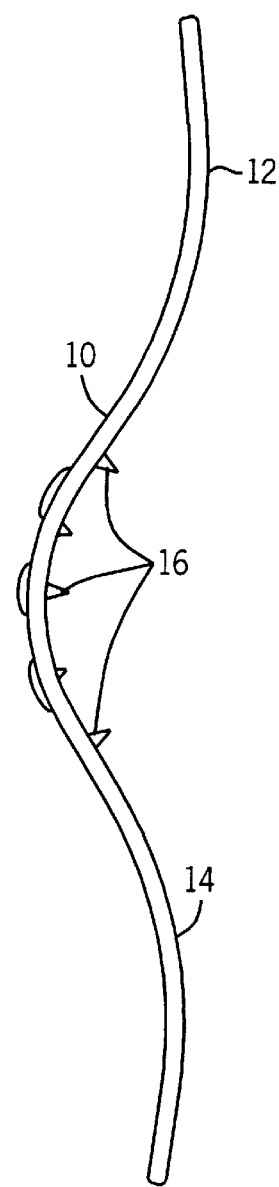
FIG. 3 is a side view of the bone plate in FIG. 1.

Referring particularly to FIGS. 2 and 3, the acetabular bone plate 5 is comprised of a central, support portion 10 disposed between integrally formed tab portions 12 and 14. The bone plate 5 is preferably formed of a titanium alloy to allow postoperative MR imaging of the joint. Stainless steel may also be used, but this limits the use of subsequent MR imaging which may become necessary to diagnose postoperative complications.

Figure 1:
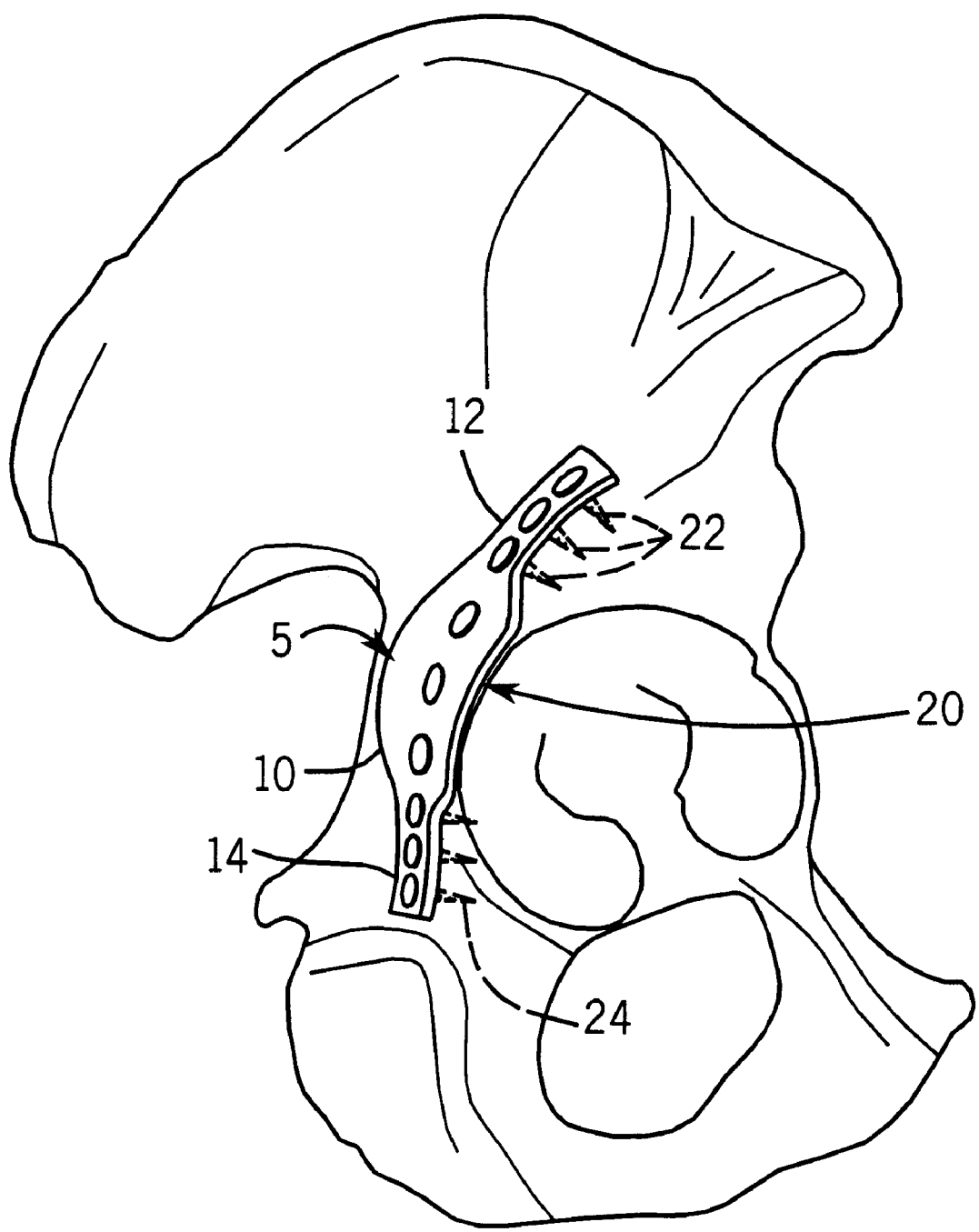
FIG. 1 is a pictorial representation of the preferred embodiment of a bone plate which practices the present invention attached to the pelvis.

The support portion 10 of the bone plate 5 has a width that is approximately twice the width of the tab portions 12 and 14. It is also about twice the width of currently available bone plates. As shown best in FIG. 3, the support portion 10 is curved to wrap around the circular-shaped posterior acetabulum wall. As shown best in FIG. 1, the support portion 10 substantially covers the posterior acetabulum wall 20, from its rim to its base. One tab portion 12 is secured in place on the pelvis by up to three small (i.e. 3.5 or 4.0 mm) fragment screws 22, and the other tab portion 14 is secured in place by up to three small fragment screws 24. The tab portions 12 and 14 can be bent as needed by the physician to fit the contour of the bone surface. The central, support portion 10 is thus firmly fixed in place to provide support for substantially the entire posterior wall 20.

Figure 4:
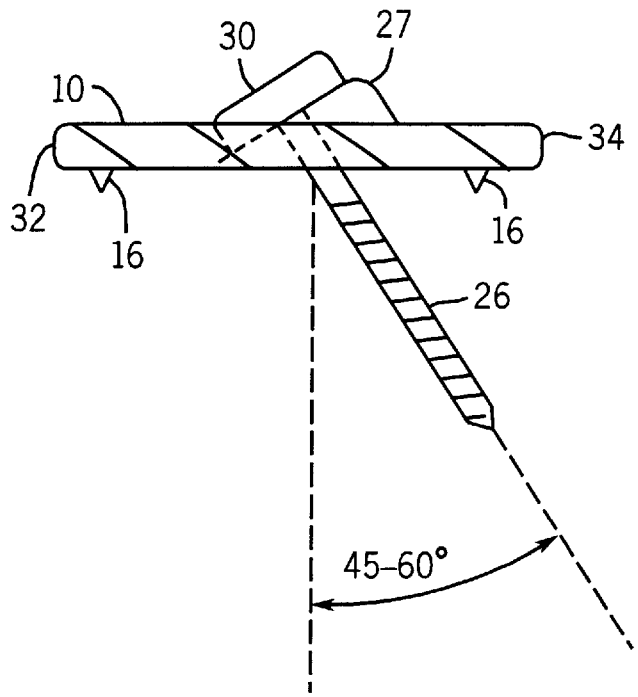
FIG. 4 is a view in cross-section through a central portion of the bone plate of FIG. 1.

Bone fragments formed by fractures in the posterior acetabulum wall are fixed to the bottom surface of the support portion 10. This is achieved by a set of from one to three small fragment screws 26 which pass through openings 28 in the support portion 10 and into the underlying bone. As shown best in FIG. 4, a buttress 27 is formed to one side of each opening 28 and the openings 28 are formed at an angle of from 45° to 6° from perpendicular. This enables the fragment screws 26 to be inserted at an angle such that their ends extend away from the hip joint preventing accidental joint penetration. The underside of each screw head 30 engages the sloped surface of the buttress 27 to securely tighten the central portion 10 against the bone surface and fix bone fragments in place.

Figure 5:
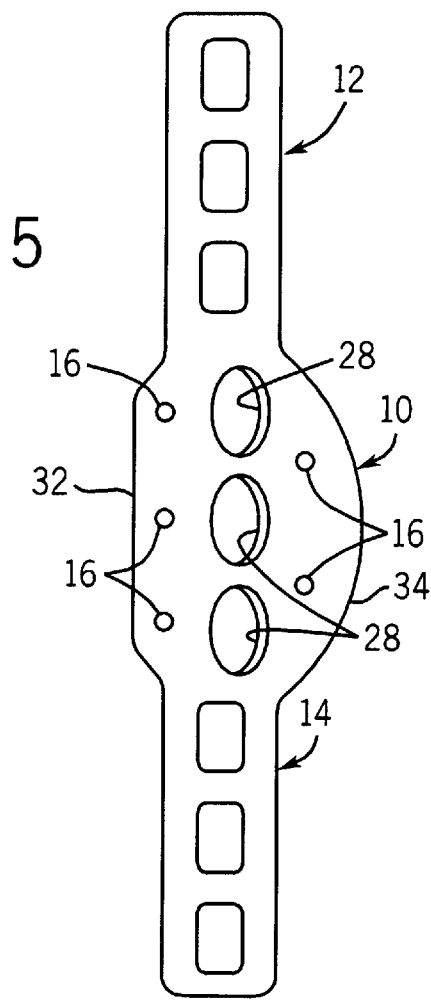
FIG. 5 is a bottom view of the bone plate of FIG. 1.

As shown best in FIGS. 3 and 5, a set of spikes 16 are formed on the underside of the support portion 10. These spikes 16 pierce the underlying bone when the bone plate 5 is fastened in place with screws 22, 24 and 26. They serve to fix to the support portion 10 underlying bone fragments. In the preferred embodiment three spikes 16 are formed along a straight edge 32 of the support portion 10, which extends along the rim of the acetabulum wall. These rim spikes 16 are very useful in fixing small comminuted and small rim fractures. Another set of spikes 16 are located near the opposite, curved edge 34 of the support portion 10. These spikes 16 engage near the base of the acetabulum. These spikes also prevent displacement of the underlying fracture fragments when the screws are tightened, driving the spikes into the underlying bone.

Referring particularly to FIG. 2, the acetabulum bone plate 5 is symmetrical about a central axis 36. As a result, the same bone plate 5 can be used on either the right or left side of the hip simply by rotating it 180° such that the straight edge 32 aligns with the rim of the acetabulum wall.

The acetabular bone plate 5 facilitates the repair of fractures. Because of its shape, a single bone plate 5 may be used to fix multiple fragments. The support portion 10 is shaped and sized to provide mechanical support for the entire posterior wall of the acetabulum. The use of a single device to make such repairs saves considerable operating time.

What is claimed is:

1. A bone plate for attachment to the acetabulum wall of a subject which comprises:
    a support portion formed from metal and curved in shape to wrap around a portion of the acetabulum wall, and having a width sufficient to cover a posterior region of the acetabulum wall extending substantially from its rim to its base;
    a pair of tabs integrally formed with the support portion and extending from opposite ends thereof, the tabs each having a width substantially less than the width of the support portion and each having openings for receiving bone screws that fasten the tabs to bone surface adjacent the acetabulum wall; and
        wherein the support portion includes openings for bone screws that fasten the support portion to the acetabulum wall.

2. The bone plate as recited in claim 1 in which the support portion and the tabs are formed from titanium.

3. The bone plate as recited in claim 1 which includes spikes integrally formed on the bottom surface of the support portion and extending away therefrom to engage and penetrate the acetabulum wall when the support portion is fastened in place.

4. The bone plate as recited in claim 3 which includes a plurality of spikes located along an edge of the support portion which extends along the ridge of the acetabulum wall.

5. The bone plate as recited in claim 4 in which the openings in the support portion are shaped to direct the bone screws therein away from the hip joint defined by the acetabulum wall.

6. The bone plate as recited in claim 5 in which the support portion, tabs and spikes are formed from titanium.

7. A bone plate for attachment to the acetabulum wall of a subject which comprises:
    a support portion formed from metal and curved in shape to wrap around a portion of the acetabulum wall, and having a width sufficient to cover a posterior region of the acetabulum wall extending substantially from its rim to its base;
    a pair of tabs integrally formed with the support portion and extending from opposite ends thereof, the tabs each having a width substantially less than the width of the support portion and each having openings for receiving bone screws that fasten the tabs to bone surface adjacent the acetabulum wall;
        wherein the support portion includes openings for bone screws that fasten the support portion to the acetabulum wall; and
        wherein a buttress is formed along one side of the openings in the support portion to direct the bone screws therein away from the hip joint defined by the acetabulum wall.

8. A bone plate for attachment to the acetabulum wall of a subject which comprises:
    a support portion formed from metal and curved in shape to wrap around a portion of the acetabulum wall, having a substantially straight edge which is positioned along the rim of the acetabulum wall and a curved edge which is positioned near the base of the acetabulum wall, and having a width sufficient to cover a posterior region of the acetabulum wall extending substantially from its rim to its base;
    a pair of tabs integrally formed with the support portion and extending from opposite ends thereof, the tabs each having a width substantially less than the width of the support portion and each having opening for receiving bone screws that fasten the tabs to bone surface adjacent the acetabulum wall; and
        wherein the support portion includes openings for bone screws that fasten the support portion to the acetabulum wall.

9. A bone plate for attachment to the acetabulum wall of a subject which comprises:
    a support portion formed from metal and curved in shape to wrap around a portion of the acetabulum wall, and having a width sufficient to cover a posterior region of the acetabulum wall extending substantially from its rim to its base;
    a pair of tabs integrally formed with the support portion and extending from opposite ends thereof, the tabs each having a width substantially less than the width of the support portion and each having openings for receiving bone screws that fasten the tabs to bone surface adjacent the acetabulum wall;
        wherein the support portion includes openings for bone screws that fasten the support portion to the acetabulum wall; and
        wherein a buttress is formed along one side of the openings in the support portion to direct the bone screws passing therethrough at an angle from 45° to 60° away from perpendicular.

* * * * *